(12) United States Patent
Smith

(10) Patent No.: US 6,596,778 B1
(45) Date of Patent: Jul. 22, 2003

(54) β-ENDORPHIN PEPTIDES FOR TREATING MUSCLE-WASTING DISEASES

(75) Inventor: Margaret E Smith, Birmingham (GB)

(73) Assignee: The University of Birmingham, Birmingham (GB)

( * ) Notice: Subject to any disclaimer, the term of this patent is extended or adjusted under 35 U.S.C. 154(b) by 0 days.

(21) Appl. No.: 09/380,169

(22) PCT Filed: Feb. 26, 1998

(86) PCT No.: PCT/GB98/00616

§ 371 (c)(1),
(2), (4) Date: Nov. 26, 1999

(87) PCT Pub. No.: WO98/38215

PCT Pub. Date: Sep. 3, 1998

(30) Foreign Application Priority Data

Feb. 28, 1997 (GB) ............................................. 9704174

(51) Int. Cl.[7] ........................ A01N 25/00; C07K 16/00; C07K 5/00
(52) U.S. Cl. ............................. 514/809; 514/2; 514/12; 530/302
(58) Field of Search ................................. 530/300, 350, 530/325, 324, 302; 514/2, 12, 14, 809

(56) References Cited

PUBLICATIONS

Khan et al., Effect of beta–endorphin 1–27 and beta–endorphin 30–31 on the contractile responses of mouse diaphragm in vitro, Journal of Physiology, vol. 487, p. 163P, 1995.*

Khan et al., Action of beta–endorphin peptides on the contractions of mouse diaphragm muscle, Peptides, vol. 18, No. 1, pp. 8787–8792, 1997.*

Smith et al., Effect of beta–endorphin and alpha–melanotropin on muscle wasting in mice, Journal of Neurological Sciences, vol. 129, Suppl., pp. 127–130, 1995.*

Protein Information Resource (PIR) accession No. I51630, 1997.*

Patent Abstracts of Japan vol. 017, No. 067 (C–1025), Feb. 10, 1993 & JP 04 273896 A (Taisho Pharmaceut Co Ltd.), Sep. 30, 1992.

Effect of beta–endorphin 1–27 and beta–endorphin 30–31 on the contractile responses of mouse diaphragm in vitro: J. Physiol., vol. 487, 1995, p. 163P XO002069247, Kahn et al.

:Action of beta–endorphin peptides on the contractions of mouse diaphragm muscle Peptides, vol. 18, No. 1, 1997. pp. 87–92, XP002069248, Khan et al.

"Effect of beta–endorphin and alpha–melanotropin on muscle wasting in mice", J. Neurological Sciences. vol. 129, No. Suppl. 1995. pp. 127–130, XP002069249.

\* cited by examiner

*Primary Examiner*—Karen Cochrane Carlson
(74) *Attorney, Agent, or Firm*—Andrus, Sceales, Starke & Sawall, LLP

(57) ABSTRACT

An active β-endorphin fragment or an analog of such a fragment is provided to a patient for alleviating the effect of muscle-wasting disease and for inhibiting or reducing leakage of an enzyme from a living muscle. The β-endorphin fragment is selected from β-endorphin (30, 31), β-endorphin (29–31), β-endorphin (28–31) and stabilized analogs thereof.

10 Claims, 2 Drawing Sheets

β-ENDORPHIN PEPTIDES FOR TREATING MUSCLE-WASTING DISEASES

CROSS-REFERENCE TO RELATED APPLICATIONS

This application is the U.S. national stage application of International Application PCT/GB98/00616, filed Feb. 26, 1998, which international application was published on Sep. 3, 1998, as International Publication WO 98/38215 in the English language. The International Application claims priority of Great Britain Patent Application 9704174.3 filed Feb. 28, 1997.

BACKGROUND AND SUMMARY OF THE INVENTION

This invention relates to an agent for alleviating the effects of muscular dystrophy and other muscle-wasting diseases (eg. motor neurone disease) in which there is leakage of enzymes such as creatine phosphokinase (CPK) from the muscle into the blood (hereinafter simply called "a muscle-wasting disease").

The present invention resides in the use of an agent which is an active β-endorphin fragment or an analogue of such a fragment, in the manufacture of a medicament for alleviating the effects of muscle-wasting disease.

The present invention also resides in the use of an agent which is an active β-endorphin fragment or an analogue of such a fragment, in the manufacture of a medicament for inhibiting or reducing leakage of an enzyme (preferably CPK) from a living muscle.

The present invention also resides in the use of an agent which is an active β-endorphin fragment or an analogue of such a fragment, in the manufacture of a medicament for improving the contractile response of muscle.

β-Endorphin is a 31 amino acid peptide which is processed in vivo by cleavage of basic amino acid residues to β-endorphin$_{1-7}$, and it has been assumed that cleavage of adjacent basic residues results in the production of the C-terminal dipeptide, β-endorphin$_{30-31}$.

The effect of these active β-endorphin fragments is particularly surprising because it has previously been observed (see Smith, M. E. and Hughes, S., "The Effect of β-Endorphin and α-Melanotropin on Muscle Wasting in Mice", Journal of the Neurological Sciences (1995),129 (suppl.), p127) that intravenous injection of β-endorphin alone produced little effect in preventing CPK leakage into the blood.

Suitable active β-endorphin fragments for use in the present invention are fragments at the C-terminal end of the β-endorphin molecule, such as β-endorphin (30–31; glycylglutamic acid), (29–31) and (28–31). In β-endorphin, the amino acids 28, 29, 30 and 31 are lysine, lysine, glycine and glutamic acid (human) or glutamine (most other mammals), respectively.

As far as the analogues of the above active β-endorphin fragments are concerned, stabilised analogues thereof are preferred wherein one or more of the following substitutions may be made:

| Amino Acid | Substituting moiety |
|---|---|
| 28 (Lys) | Orn, MeLys, des-NH$_2$, Nle or D-Lys |
| 29 (Lys) | Orn, D-Lys, MeLys or Nle |
| 30 (Gly) | Sar, AzGly, Ala, D-Ala, D-Ser or Pro |
| 31 (Glu) | Gln. |

Additionally, the hydrogen terminating the N-terminal end (preferably the β-endorphin 28-amino acid-N-terminal) of the β-endorphin fragment may be substituted by Ac, β-Ala, HOOC(CH$_2$)$_2$CO—, Tyr, benzylcarbonyl (C$_6$H$_5$CH$_2$CO—), malonyl or R (wherein Ac is an acyl group, for example acetyl, and R is a fatty acyl group.

Of such analogues, those where amino acid 30 (Gly) is replaced by Sar, those where amino acid 29 (Lys) is replaced by D-Lys, and those where the N-terminal (28) end of the fragment is Ac-Lys, are preferred. Particularly preferred is the stabilised analogue in which all three substitutions have been made, i.e. Ac-Lys-D-Lys-Sar-Glu, most preferably CH$_3$CO-Lys-D-Lys-Sar-Glu.

Furthermore, the above C-terminal peptides (i.e. the above-mentioned β-endorphin fragments are small molecules compared to β-endorphin and analogues of these fragments can be made which are stable to proteolytic digestion and therefore have a relatively long half-life in the blood enabling their actions to be long lasting. Their resistance to proteolytic digestion may also make them effective via oral administration. In addition, the C-terminal peptides do not contain the opioid amino acid sequence and therefore are not likely to have the side effects of β-endorphin which are due to its opioid actions.

Thus, it is considered that the active β-endorphin fragments and analogues thereof may be administered intravenously, subcutaneously or intramuscularly, although stabilised analogues, such as Ac-Lys-D-Lys-Sar-Glu, may possibly be administered orally.

In one series of experiments, the C-terminal peptide, glycylglutamine, was injected intravenously into the blood of dystrophic mice 4 to 5 times a week in an amount of approximately 1.5 microgram/g body weight each time over a seven week period. Control mice were injected with the same volume of saline at the same times. There were six mice in each group.

The following measurements were made:
1. Change in body weight (the dystrophic mice would usually not gain significant weight over seven weeks and might even lose weight-depending on their age).
2. Weight of the extensor digitorum longus (EDL) muscle.
3. Level of CPK in the blood (a diagnostic test for muscular dystrophy is to measure the level of CPK in the blood. In muscle diseases, the blood levels of enzymes such as CPK are elevated and in muscular dystrophy the levels can be very high).
4. CPK enzyme levels in the muscle.

The following results were obtained:
1. The mice treated with glycylglutamine showed a statistically significant increase in body weight (of approximately 12%), whilst the saline controls showed a slight decrease in body weight (0.04% which is non-significant).
2. There were slight increases in EDL muscle weight (approximately 5%) which were not statistically significant.

3. The CPK level in the blood was reduced by 25%, indicating an improvement in the health of the muscle (i.e. less damage).
4. The enzyme concentration in the EDL muscle was increased by 55% (when calculated on a wet weight basis).

The above findings, particularly in result 4 above, indicate that chronic injections of this peptide could be therapeutic in muscular dystrophy. In Duchenne muscular dystrophy—the most common muscular dystrophy in humans—it appears to be the fast muscle fibres which are most involved in the disease process. The muscle examined (the EDL) is a fast muscle which contains a high proportion of fast fibres.

The effects of different β-endorphin-derived peptides on the contractile responses in mouse diaphragm muscle have been further examined in order to see which regions of the parent molecule might be important for its effect.

Naloxone was added to give a concentration of ($2.5 \times 10^{-6}$ M). BNTX or NTB were added to give a concentration of ($2.5 \times 10^{-7}$ M) in either case.

Figure 4:
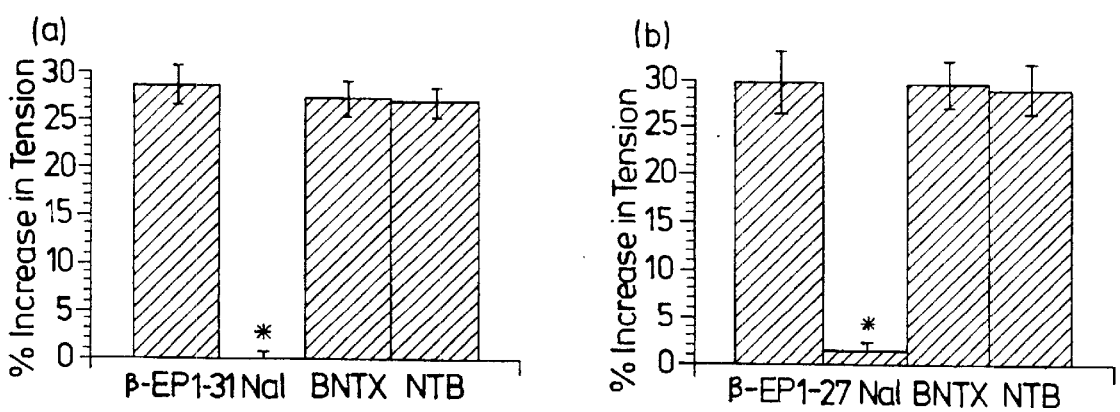
Figure 4:
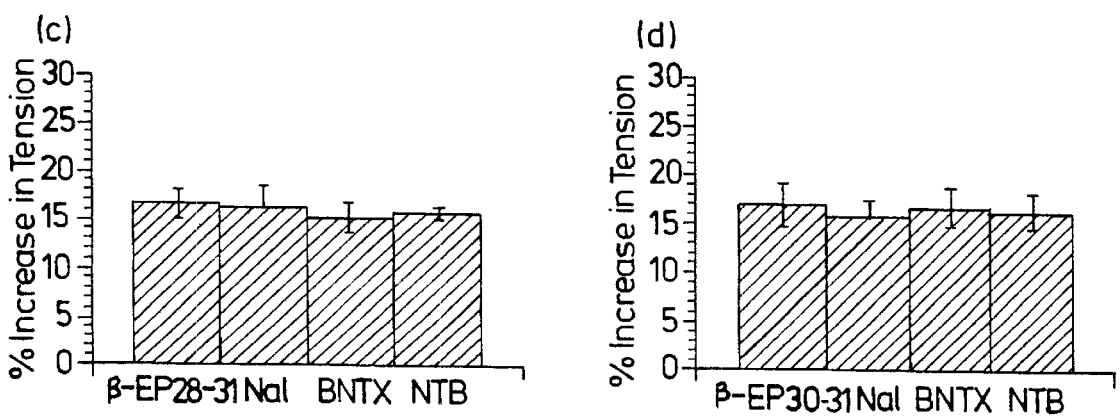

The results are expressed as the means±S.E.M. (bars) for at least 4 experiments in each case (*p<0.05); and FIG. 4 shows the effect of opioid antagonists on the actions of β-endorphin derivatives to increase the contractile responses. (a) β-endorphin, (b) β-endorphin$_{1-27}$, (c) β-endorphin$_{28-31}$ analogue, (d) glycyl-L-glutamine. The peptides were present in concentrations of $2.5 \times 10^{-7}$ M in each case. Naloxone was added to give a concentration of ($2.5 \times 10^{-6}$ M). BNTX or NTB were added to give a concentration of ($2.5 \times 10^{-7}$ M) in either case. The results are expressed as the means±S.E.M. (bars) for at least 4 experiments in each case (*p<0.05).

The results shown in the drawings were obtained in the following experiments:

DETAILED DESCRIPTION OF THE INVENTION

EXPERIMENTS

Adult female mice, 3–4 months of age, of the C57BL/6j strain were killed by cervical dislocation and the skin and musculature around the rib cage were removed. The diaphragm and part of the rib cage were carefully dissected out along with a length of the left phrenic nerve. The left hemidiaphragm (together with the left phrenic nerve stump) was pinned out in an organ bath containing oxygenated Krebs solution which was gassed continuously with 95% $O_2$–5% $CO_2$ at room temperature (approximately 20° C.) as described in Khan, S.; Smith, M. E., Muscle Nerve, 18, 1250–1256; 1995. The central tendon was attached with the aid of a silk thread to a force transducer (Dynamometer, model UF1), and the phrenic nerve was introduced into the end of a suction electrode for indirect stimulation.

The phrenic nerve was stimulated continuously at a low frequency (0.5 Hz) with supramaximum square wave pulses of 0.2 msec width using a dual channel stimulator (Digitimer D4030). The muscle was allowed to equilibrate until the responses of the stimulated muscle had reached a constant amplitude (approximately 20 min). Krebs solution (100 ml), or a solution (100 ml) of the appropriate peptide, was added to the centre of the organ bath whilst the contractions were being recorded.

Direct stimulation of the muscle was effected by two stainless steel needle electrodes placed near the centre of the hemidiaphragm. The position of the force transducer was adjusted until a constant resting tension was seen. When direct stimulation of the muscle was employed d-tubocurarine chloride ($2.5 \times 10^{-6}$ M) was included in the bathing medium to block the acetylcholine (ACh) receptors and prevent indirect stimulation of the muscles via the motor nerve terminals. The phrenic nerve was stimulated continuously at 0.5 Hz, d-tubocurarine was added to the organ bath, and then, when the responses to nerve stimulation had ceased, the muscle was subjected to continuous direct supramaximum stimulation at a frequency of 0.5 Hz. The tension produced during the experiments was amplified and displayed on a digital recording oscilloscope (Gould 1602), recorded on an Apple Macintosh computer (IICi) and analyzed off-line. The amplitude, time to peak and half relaxation time of the contractions developed in response to indirect and direct stimulation were determined. The half-relaxation time of the contractions was expressed as the time taken for the tension to decline from the maximum amplitude to half maximum. The dose-response curves were analyzed using a Kaloidograph software package to determine the values for $EC_{50}$ and maximum response. The significance of the results was determined, unless otherwise stated, using ANOVA, with treatment as the grouping factor, followed by the Bonferroni-Dunn post hoc test.

RESULTS

Effect of β-endorphin and Derivatives

Figure 1:
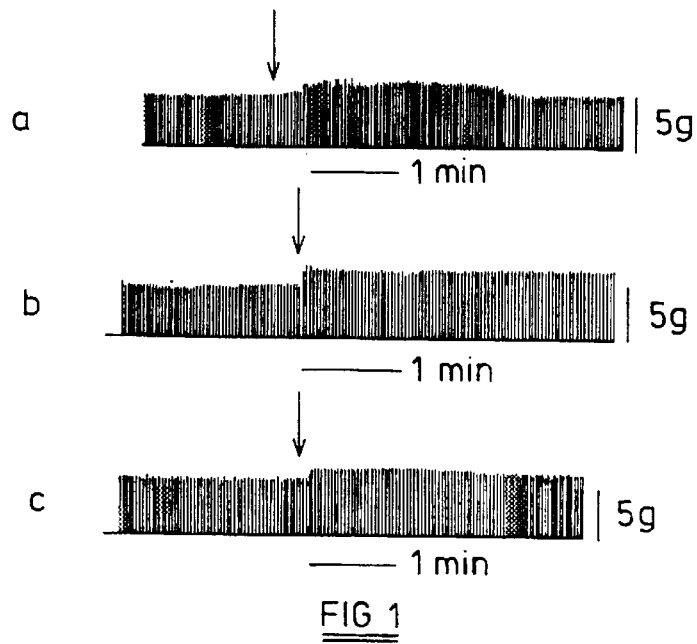
FIG. 1 shows typical experimental recordings of contractions of hemidiaphragm muscle developed in response to stimulation of the phrenic nerve. Effect of (a) β-endorphin$_{1-27}$ ($2.5 \times 10^{-9}$ M), (b) β-endorphin$_{28-31}$ analogue ($2.5 \times 10^{-8}$ M) and (c) glycyl-L-glutamine ($2.5 \times 10^{-8}$ M) added at the arrows.
Figure 2:
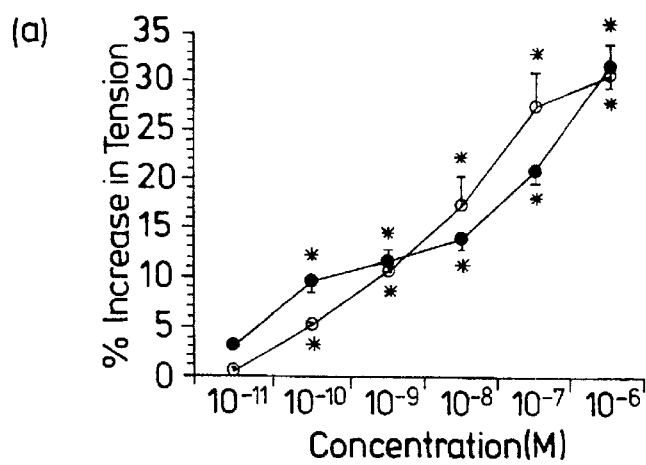
FIG. 2 shows the effect of different concentrations of (a) β-endorphin (open symbols) and β-endorphin$_{1-27}$ (closed symbols) and (b) glycyiglutamine (open symbols) and β-endorphin$_{28-31}$ analogue (closed symbols), on the amplitude of contractions developed in response to low frequency stimulation of the nerve. The values are the maximum responses and are given as the means±S.E.M. for at least 5 experiments in each case (*p<0.05)
Figure 2:
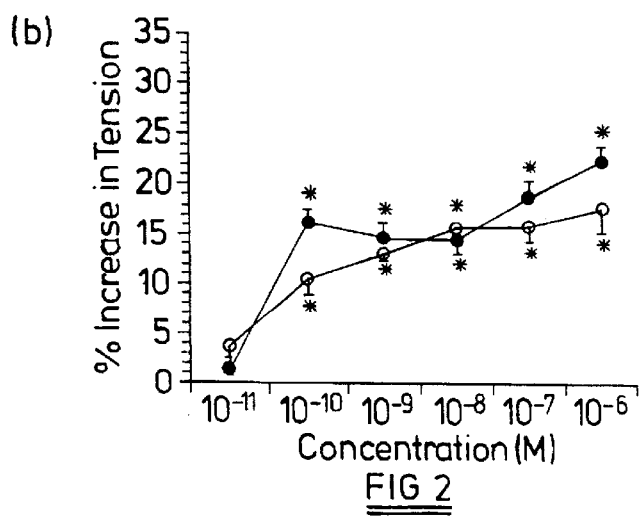

When skeletal muscles were stimulated continuously at 0.5 Hz via the phrenic nerve, the contractions elicited, after the initial equilibration period, were of constant amplitude for at least 1 hour. When β-endorphin, β-endorphin$_{1-27}$, glycylglutamine or the β-endorphin$_{28-31}$ analogue was applied to the organ bath, an immediate increase in the amplitude of the contractions was seen. FIG. 1 shows typical experimental recordings from experiments where β-endorphin$_{1-27}$, or the C-terminal peptides were added to the organ bath. The effect of β-endorphin$_{1-27}$ was short-lived, and the amplitude of the responses had declined to the initial level by 2 to 3 minutes after the addition of the peptide. FIG. 2(a) shows the effects of different concentrations of β-endorphin or β-endorphin$_{1-27}$ on the responses. Analysis of the concentration response curve indicated an $EC_{50}$ of $5 \times 10^{-9}$ M for β-endorphin and a maximum increase in the response of 34.4±2.9 (SEM) %. The effect of β-endorphin$_{1-27}$, however was not maximum even at $10^{-6}$ M. β-Endorphin 1–16 (α-endorphin) had no significant effect on the amplitude of the responses. In the presence of the latter peptide at a concentration of $10^{-6}$ M, the tension developed was 102.0±0.2% of the control tension. N-Acetyl β-endorphin also had no significant effect. In the presence of this peptide, the responses were 101.5±0.7 (SEM) % for three preparations.

Typical experimental recordings showing the effects of glycyl-L-glutamine and the β-endorphin 28–31 analogue are shown in FIGS. 1(b) and (c), respectively. The effects of the synthetic analogue and glycylglutamine were more sustained than those of β-endorphin or β-endorphin$_{1-27}$. The effect of the analogue was maintained for at least 6 minutes (not shown). This may reflect its slower proteolytic degradation. FIG. 2(b) shows the effects of different concentrations of the β-endorphin C-terminal peptides on the contractile responses of the diaphragm muscle to indirect stimulation. Both glycyl-L-glutamine and the β-endorphin$_{28-31}$ analogue caused significant, concentration-dependent, increases in the contractile responses. Furthermore, significant increases were seen at concentrations as low as $10^{-10}$ M with both peptides.

In control experiments, L-glutamic acid had no effect on the amplitude of the contractile responses. Analysis of the concentration response curves showed that the glycyl-glutamine and the β-endorphin$_{28-31}$ analogue were both more potent than β-endorphin itself (with $EC_{50}$ values less than $10^{-10}$M), although the maximum increases seen with the peptides were less than those seen with β-endorphin. The maximum increases were 18.5±1.5 (SEM) % and 16.7±0.9 (SEM) % for glycyl-L-glutamine and the β-endorphin 28–31 analogue respectively.

Effect on the Time Course of the Contractions

There was no significant effect of β-endorphin$_{1-27}$ on the time to peak of the contractions developed in response to indirect stimulation, but both β-endorphin and the β-endorphin$_{28-31}$ analogue caused a significant reduction in the time to peak (see Table below). None of the peptides had any significant effect on the half-relaxation time of the contractions

TABLE

Effect of β-endorphin, β-endorphin$_{1-27}$ and MPF analogue on the time course of the responses to low frequency indirect stimulation.

| Peptide | Time to peak | p | 1/2 relaxation time | n | p |
|---|---|---|---|---|---|
| β-EP | 94.1 ± 0.5 | <0.002 | 99.6 ± 0.3 | 6 | NS |
| β-EP$_{1-27}$ | 98.1 ± 0.4 | NS | 99.4 ± 0.4 | 5 | NS |
| β-EP$_{28-31}$* | 95.9 ± 0.3 | | | <0.01 | |
| 102.8 ± 2.6 | | 5 | NS | | |

The peptides were added to give a concentration of $2.5 \times 10^{-7}$ M. The results are given as a percentage of the untreated controls. The values are given as the means±S.E.M., n is the number of experiments. p, the probability level compared to the responses in untreated preparations, was determined using Student's t-test. (* β-Endorphin$_{28-31}$ analogue)

Effect of Opioid Ligands

Figure 3:
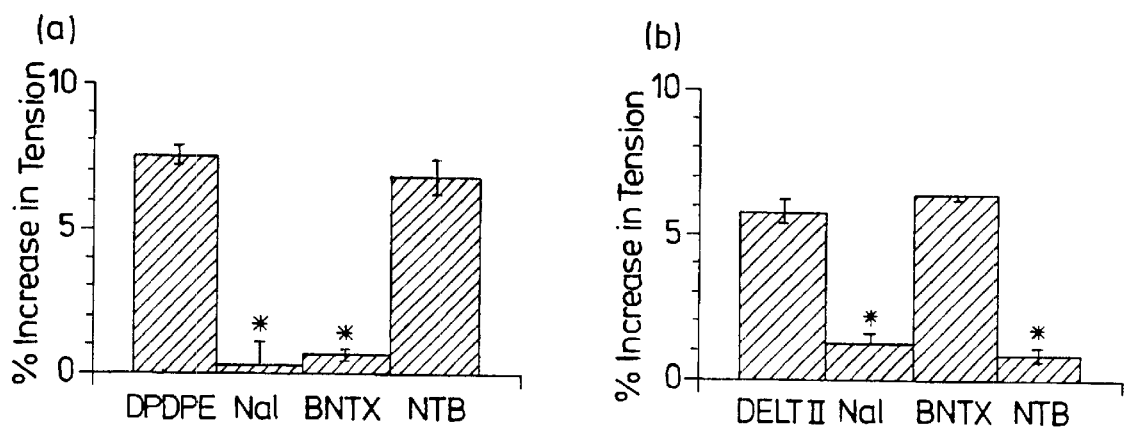
FIG. 3 shows the effect of d-opioid antagonists on the actions of d-opioid agonists to increase the contractile responses. (a) DPDPE, (b) deltorphin II. The agonists were present in concentrations of $2.5 \times 10^{-7}$ M.

In Khan, S.; Smith, M. E., Muscle Nerve, 18, 1250–1256; 1995 (supra), it was shown that both [D-penicillamine$^2$,D-penicillamine$^5$] enkephalin (DPDPE), a $d_1$-opioid agonist, and, a $d_2$ agonist (19), caused small but significant increases in the contractile responses to indirect stimulation. The $EC_{50}$ values obtained after analysis of the dose response curves were $2 \times 10^{-11}$ M and $2 \times 10^{-10}$ M for DPDPE and deltorphin II respectively. The maximum increases were 5.5±0.3 (S.E.M.) % and 2.4±0.3 (SEM) % for DPDPE and deltorphin II respectively. The selective $d_1$-opioid antagonist 7-benzylidene naltrexone (BNTX, 23) in a concentration of $2.5 \times 10^{-7}$ M blocked the potentiating action of DPDPE and the selective $d_2$-opioid antagonist naltriben (NTB, 24), in a concentration of $2.5 \times 10^{-7}$ M, blocked the potentiation produced by deltorphin II (FIG. 3), indicating that the effects of the two agonists were probably via their respective d-opioid receptor subtypes. When both d-opioid agonists were present together in concentrations in each case of $2.5 \times 10^{-7}$ M (which gave maximum increases with each agonist alone) there was no additive effect, indicating the possibility that the agonists were binding to the same receptor.

When β-endorphin$_{1-27}$ (which contains the N-terminal opioid sequence of β-endorphin) was added to preparations incubated in the presence of the opioid antagonist naloxone at a concentration of $2.5 \times 10^{-6}$ M (which had previously been shown to produce complete blockade of the effect of β-endorphin itself), it had no effect on the amplitude of the contractions developed in response to stimulation of the nerve indicating that the action of this peptide was opioid in nature (FIG. 4). However, neither the $d_1$-opioid antagonist BNTX nor the $d_2$-opioid antagonist NTB in concentrations of $2.5 \times 10^{-7}$ M (which blocked the effects of the respective d-opioid agonists, see FIG. 3) produced any blockade of the effects of β-endorphin or β-endorphin$_{1-27}$ (FIG. 4).

Neither naloxone, BNTX, nor NTB blocked the effects of glycyl-L-glutamine or the β-endorphin$_{28-31}$ analogue (FIG. 4), both of which lack the opioid sequence.

Effect of the Peptides in the Presence of Neostigmine Sulphate

When the preparations were incubated in the presence of the anticholinesterase neostigmine sulphate ($10^{-5}$ M), neither β-endorphin$_{1-27}$ nor the β-endorphin$_{28-31}$ analogue had any effect on the amplitude or time course of the contractions developed in response to stimulation of the nerve. When the peptides were added in a concentration of $10^{-7}$ M the tension developed was 102.3±1.2 (S.E.M.) % and 103.4±1.0 (S.E.M.) % in the presence of β-endorphin$_{1-27}$ and the β-endorphin$_{28-31}$ analogue respectively.

Effect of Peptides on the Contractions Developed in Response to Direct Stimulation of the Muscle.

Neither β-endorphin$_{1-27}$, nor the β-endorphin$_{28-31}$ analogue, nor glycyl-L-glutamine had any significant effect on the amplitude or time course of the contractions developed in response to direct stimulation of the muscle in the presence of d-tubocurarine. When the peptides were present in a concentration of $2.5 \times 10^{-8}$ M in each case, the tension developed, compared to that recorded in the absence of added peptide, was 99.6±0.5 (S.E.M.) %, 100±1.1 (S.E.M) % and 98.7±0.9 (S.E.M.) % of the control values for β-endorphin$_{1-27}$, β-endorphin$_{28-31}$ analogue and glycyl-L-glutamine respectively.

The above results show that various derivatives of β-endorphin, like the parent peptide itself, increase the amplitude of contractions in diaphragm skeletal muscle in response to stimulation of the phrenic nerve. At least two regions of the β-endorphin molecule may be important for the potentiation of the responses, one of these being a region present in β-endorphin$_{1-27}$ and the other the C-terminal dipeptide.

β-Endorphin$_{1-27}$ contains the opioid sequence and its effect may therefore be via an opioid receptor. β-Endorphin$_{1-16}$ was ineffective, but some opioid fragments of β-endorphin are subject to rapid hydrolysis and this may account for the lack of effect of this compound.

C-Terminal derivatives of β-endorphin were more potent than β-endorphin$_{1-27}$ or β-endorphin in increasing the contractile responses. Furthermore the C-terminal$_{28-31}$ analogue decreased the time to peak, whilst the β-endorphin$_{1-27}$ derivative did not. However the C-terminal derivatives did not alter the half relaxation time. The reasons for this effect are unclear at present but one possibility is that the peptides have some effect to preferentially increase ACh levels at the neuromuscular junctions of fast muscle fibers. The mouse diaphragm consists of a mixture of slow oxidative, fast oxidative and fast glycolytic fibers. If fast fibers were recruited sooner in the presence of the peptide, this could increase the time to peak without altering the half-relaxation time as the latter depends on the slow contracting fibers.

The effects of the C-terminal derivatives which do not contain the opioid sequence were not blocked by naloxone. Thus β-endorphin may increase the contractile responses by mechanisms involving the activation of multiple receptors, including one which binds the C-terminal sequence. However the actions of both β-endorphin and the C-terminal derivatives were not apparent in the presence of neostigmine and the peptides had no effect if the muscles were stimulated triggered at some junctions in response nerve impulses. The preparation used here at room temperature may therefore mimic physiological situations where neuromuscular transmission may not be efficient such as during strenuous exercise when ACh in the nerve terminals is relatively depleted, or in development or in pathological conditions involving defects at the neuromuscular junction. The actions of β-endorphin at the neuromuscular junction might then be important. It is interesting in this respect that it has been shown that β-endorphin is released into the blood from the pituitary during strenuous exercise and that it is present in intramuscular motor nerves in development and in pathological conditions in rodents. The biological half-lives of attenuated derivatives of β-endorphin derivatives in the blood or the neuromuscular cleft are unknown, but it is possible that products of β-endorphin degradation can also contribute under some circumstances to the efficiency of neuromuscular transmission in vivo.

SEQUENCE LISTING

```
<160> NUMBER OF SEQ ID NOS: 1

<210> SEQ ID NO 1
<211> LENGTH: 31
<212> TYPE: PRT
<213> ORGANISM: Homo sapien
<300> PUBLICATION INFORMATION:
<302> TITLE: The Primary Structure of Identified Opioid Peptides of
      Natural Origin
<303> JOURNAL: Opioid Peptides
<304> VOLUME: III
<306> PAGES: 48-48
<307> DATE: 1983
<308> DATABASE ACCESSION NUMBER: ISBN 0-8493-6237-7
<309> DATABASE ENTRY DATE: 1983-12-31
<300> PUBLICATION INFORMATION:
<302> TITLE: Endorphins
<303> JOURNAL: The Merck Index
<305> ISSUE: 10th
<306> PAGES: 3534-3535
<307> DATE: 1983
<308> DATABASE ACCESSION NUMBER: ISBN 911910-27-1
<309> DATABASE ENTRY DATE: 1983-12-31

<400> SEQUENCE: 1

Tyr Gly Gly Phe Met Thr Ser Glu Lys Ser Gln Thr Pro Leu Val Thr
 1               5                  10                  15

Leu Phe Lys Asn Ala Ile Ile Lys Asn Ala Tyr Lys Lys Gly Glu
            20                  25                  30
``` directly. Thus the site of action for both β-endorphin$_{1-27}$ and the C-terminal peptides is probably the neuromuscular junction. One possible explanation is that their effects are due to inhibition of AChE. Indeed inhibition of AChE activity by β-endorphin and β-endorphin$_{1-27}$ has been reported in other species. Moreover, it has also been shown that radiolabelled β-endorphin binds specifically to a purified preparation of endplate-specific AChE. However, no evidence has been reported that C-terminal derivatives of β-endorphin inhibit AChE.

Neuromuscular transmission is not always efficient at room temperature and the actions of the peptides at the neuromuscular junction could cause a reduction in the number of failures of transmission. Alternatively, if they inhibit AChE they may cause multiple action potentials to be

What is claimed is:

1. A method of treating a patient for alleviating the effect of muscle-wasting disease, or for inhibiting or reducing leakage of an enzyme from a living muscle, comprising the step of administering to such patient an active C-terminal β-endorphin fragment or an active analogue of such a fragment wherein said fragment or analogue thereof inhibits leakage of creatine phosphokinase from living muscle.

2. The method as claimed in claim 1, wherein the active β-endorphin fragment is selected from β-endorphin (30, 31), β-endorphin (29–31) and β-endorphin (28–31).

3. The method as claimed in claim 2, wherein the active β-endorphin fragment is stabilized analogue wherein one or more of the following substitutions are made relative to a reference human β-endorphin SEQ ID No. 1:

| Amino Acid | Substituting moiety |
|---|---|
| 28 | Orn, MeLys, des-NH$_2$, Nle or D-Lys |
| 29 | Orn, D-Lys, MeLys or Nle |
| 30 | Sar, AzGly, Ala, D-Ala, D-Ser or Pro |
| 31 | Gln. |

4. The method as claimed in claim 3, wherein amino acid 30 is replaced by Sar.

5. The method as claimed in claim 3, wherein amino acid 29 is replaced by D-Lys.

6. The method as claimed in claim 1, wherein a hydrogen at the N-terminal end of the active β-endorphin fragment is substituted by Ac, β-Ala, HOOC(CH$_2$)$_2$CO—, Tyr, benzyl-carbonyl (C$_6$H$_5$CH$_2$CO—), malonyl or R (wherein Ac is an acyl group and R is a fatty acyl group).

7. The method as claimed in claim 6, wherein the fragment has four amino acids, and wherein the amino acid at the N-terminal end of the active β-endorphin fragment is Lys.

8. The method as claimed in claim 7, wherein a hydrogen of said N-terminal Lys is substituted by Ac.

9. The method as claimed in claim 1, wherein the β-endorphin fragment or analog thereof is Ac-Lys-D-Lys-Sar-Glu or CH$_3$CO-Lys-Sar-Glu.

10. A method of treating a patient for alleviating the effect of muscle-wasting disease, or for inhibiting or reducing leakage of an enzyme from a living muscle, comprising the step of administering to such patient an active C-terminal β-endorphin fragment or an active analogue of such a fragment, wherein said fragment or analogue thereof inhibits leakage of creatine phosphokinase from living muscle and said active analogue has one or more of the following substitutions relative to a reference human β-endorphin SEQ ID No. 1:

| Amino Acid | Substituting Moiety |
|---|---|
| 28 | Orn, MeLys, des-NH$_2$, Nle or D-Lys |
| 29 | Orn, D-Lys, MeLys or Nle |
| 30 | Sar, AzGly, Ala, D-Ala, D-Ser or Pro |
| 31 | Gln; | with the proviso that the analogue cannot be Gly-Gln or Ac-Lys-D-Lys-Sar-Glu-OH.

* * * * *